United States Patent
Phillips

(10) Patent No.: US 9,872,996 B2
(45) Date of Patent: Jan. 23, 2018

(54) SYSTEM AND METHOD FOR TRANSCRANIAL CURRENT LOOP BRAIN STIMULATION

(71) Applicant: James William Phillips, Fountain Valley, CA (US)

(72) Inventor: James William Phillips, Fountain Valley, CA (US)

(*) Notice: Subject to any disclaimer, the term of this patent is extended or adjusted under 35 U.S.C. 154(b) by 160 days.

(21) Appl. No.: 14/595,118

(22) Filed: Jan. 12, 2015

(65) Prior Publication Data

US 2016/0199656 A1    Jul. 14, 2016

(51) Int. Cl.
| | |
|---|---|
| *A61N 1/18* | (2006.01) |
| *A61N 1/05* | (2006.01) |
| *A61N 1/378* | (2006.01) |
| *A61N 1/36* | (2006.01) |

(52) U.S. Cl.
CPC ......... *A61N 1/3787* (2013.01); *A61N 1/0531* (2013.01); *A61N 1/3606* (2013.01); *A61N 1/36064* (2013.01); *A61N 1/36067* (2013.01); *A61N 1/36071* (2013.01); *A61N 1/36075* (2013.01); *A61N 1/36103* (2013.01); *A61N 1/36139* (2013.01); *A61N 1/36171* (2013.01); *A61N 1/0529* (2013.01); *A61N 1/0534* (2013.01); *A61N 1/36082* (2013.01)

(58) Field of Classification Search
CPC .................................. A61N 1/378; A61N 1/36
USPC .............. 607/45, 46, 72, 116, 117; 600/544
See application file for complete search history.

(56) References Cited

U.S. PATENT DOCUMENTS

| | | | |
|---|---|---|---|
| 6,205,359 B1 | 3/2001 | Boveja | |
| 6,230,049 B1* | 5/2001 | Fischell | A61B 5/0476 600/544 |
| 2003/0125786 A1* | 7/2003 | Gliner | A61N 1/0531 607/116 |
| 2006/0217782 A1* | 9/2006 | Boveja | A61N 1/0531 607/45 |
| 2010/0324623 A1 | 12/2010 | Tanaka et al. | |
| 2010/0331925 A1* | 12/2010 | Peterson | A61N 1/36071 607/72 |
| 2011/0046693 A1 | 2/2011 | Lee et al. | |
| 2011/0112602 A1 | 5/2011 | Lee et al. | |
| 2011/0137381 A1 | 6/2011 | Lee et al. | |
| 2011/0218588 A1 | 9/2011 | Jung et al. | |
| 2016/0199656 A1* | 7/2016 | Phillips | A61N 1/3787 607/45 |

* cited by examiner

*Primary Examiner* — Carl H Layno
*Assistant Examiner* — Jon Eric C Morales
(74) *Attorney, Agent, or Firm* — Wilson Sonsini Goodrich & Rosati

(57) ABSTRACT

A method and device is described, which provides electrical stimulation to the brain of a person, where the device comprises an external portion and at least one implantable portion. The external portion provides the energy source for stimulation to the implantable portions. The implantable portions provide at least two conductive paths through the skull and use the skull's high impedance to generate a current loop with the focus of stimulation lying in the current path.

19 Claims, 12 Drawing Sheets

SYSTEM AND METHOD FOR TRANSCRANIAL CURRENT LOOP BRAIN STIMULATION

CROSS-REFERENCE TO RELATED APPLICATIONS

The present application claims the benefit of provisional application 61/926,206 filed on Jan. 10, 2014, the full disclosure of which is incorporated herein by reference.

BACKGROUND OF THE INVENTION

Electric brain stimulation has been shown to be as potentially effective treatment for a number of brain disorders, including epilepsy, migraine, fibromyalgia, major depression, stroke rehabilitation, and Parkinson's disease, and is also used in electrocorticography and Cortical Stimulation Mapping (CSM). In epilepsy, the generally accepted treatment method involves locating the epileptic focus in the brain, which is found using EEG analysis of epileptiform discharges and resultant spike or seizure voltage fields at the scalp. The temporal lobe is often the location of epileptogenesis, though the position and orientation may vary between individuals. In treating major depression, the target is often the left dorsolateral prefrontal cortex. In treating migraine, the visual cortex or motor cortexes are generally targeted, as well as the occipital nerves. In stroke recovery for reduced limb movement, the area of the motor cortex associated with the limb is the usual target. Once the target site is located, electrical stimulation is applied to provide therapy for the specific indication.

Electric brain stimulation may be accomplished by several means. Repetitive Transcranial Magnetic Stimulation (TMS) is a noninvasive technique that uses a coil to deliver a series of high energy magnetic pulses to the brain, thereby inducing current to flow in the cortex underneath the coil. rTMS has been shown to be effective in the treatment of major depression, and other mental disorders. However, it is not easily directed to a particular location, and involves a large, expensive device to generate the high current pulse to the coil. rTMS is not portable and requires a treatment administrator to deliver therapy to the patient.

Transcranial Direct Current Stimulation (tDCS) uses electrodes on the outside of the head to deliver small amounts of current to the brain. tDCS was originally used for stroke recovery, and has shown promise in the treatment of some mental disorders and for cognitive improvement. Electrodes are located near the region of interest for stimulation. The vast majority of current is shunted between the electrodes since the skull is a very effective electrical insulator. However, a portion of the current does result in intracerebral current flow, which may increase or decrease neuronal excitability and alter brain function. The exact method of action is unclear. tDCS current strength is limited due to the excitability of nerves in the scalp, which can cause discomfort to the patient if the current is set too high.

Vagus nerve stimulation involves electrically stimulating the vagus nerve in the neck of the patient. This can be done either using electrodes on the skin, which may involve painful sensation of the patient, or surgically implanting electrodes near the vagus nerve, generally with a power source implanted elsewhere in the body. This involves a significant surgical procedure and has shown efficacy in treatment of epilepsy and depression.

Deep brain stimulation (DBS) uses electrodes implanted and placed bilaterally into the basal ganglia, cerebellum, anterior principal nucleus, the centromedian nucleus, caudate nucleus, thalamic, or subthalamic region. Stimulation may also be delivered subcortically. Stimulus trains are delivered for treatment of a number of disorders, including epilepsy, Parkinson's disease, and major depression. DBS is generally a very invasive procedure, requiring a long lead that penetrates the skull with multiple electrodes near the tip. The procedure is considered major surgery and is not generally used unless other methods have been exhausted.

Direct cortical stimulation (DCS) is similar to DBS, except that the lead lies on the surface of the cortex, either subdural or epidural. The location of the electrodes is generally near the seizure foci. The electrodes are secured in place using sutures. This technique often involves removing a portion of the skull to gain access to the cortical surface, and possibly to make room for the power source. DCS has been shown to have efficacy in treatment of epilepsy and neuropathic pain.

It is possible to perform electrical stimulation of the brain utilizing a current loop through a conductive path involving probes that penetrate the skull at two or more points. Since the skull is highly resistive (approximately 80 times more resistive than the cerebrospinal fluid (CSF) around the brain), it acts as a good insulator. If the area around the two probes that penetrate the skull is filled with a resistive material, like silicone, then a current source through one probe would not have a low impedance return path except through the other probe. Each probe could have an electrode at the tip, and the length, angle, and position of each probe would allow for precise stimulation of any area of the brain. A second pair of electrodes could be located subcutaneously, so that the current return path would travel through or under the scalp. The current source could be an implanted pulse generator, an ultrasonic transducer, or a coil that uses an external alternating magnetic field to induce electric current. Other current sources are also possible as well. If magnetic induction is used, the external portion could be a small case that contains a coil or rotating magnet. This would likely be not much larger than a cigarette pack and would be very light. In the case of a rotating magnet, a diametrically magnetized cylindrical magnet rotating at 500 Hz can induce a 10 mA p-p current in a 600-turn coil through a 2000 ohm load. This configuration has advantages over existing devices and methods. It allows for more precise stimulation than rTMS and the external portion is smaller and more portable. It allows for more precise stimulation than tDCS with greater stimulation current. It allows for more precise stimulation than Vagus nerve stimulation, with better understood method of action.

To implant the implantable portions, up to two small incisions are made in the scalp and small burr holes drilled in the skull (similar to trephination) at locations on opposite sides of the intended stimulation site. The probes are inserted through the burr holes. The probes contain a resistive material to fill the space in each burr hole. Both implants are pressed flat. Impedance testing or stimulation may be performed to ensure proper placement of the subcranial electrodes. The scalp is sutured and the procedure is complete. Such a procedure could be performed on an outpatient basis, with a mild anesthetic. By contrast, DCS generally involves a significant craniotomy, and the electrodes must be sutured in place to ensure migration does not occur. No electrode sutures are required for the current loop procedure, since the probes are held in place in the burr holes. DBS is a much more invasive procedure in which a lead contains multiple electrodes, and stimulation occurs between two or more of those electrodes to affect a particular region of the brain. In the present invention, current flows between the top of two probes, thereby potentially covering a larger area.

U.S. Patent Application No. 2011/0218588 (Jung) is directed at electrical stimulation of the cortex with an externally powered magnetic coil and one or more implants with coils that are powered inductively. For as single implant, a plug with 2 electrodes at the tip is used. For a pair of implants, the induced current flows from one implant, through the cortex, through the other implant and back through a wire. By specifying a wire between the two implants, this patent points away from applications such as the current application, which makes use of the skull's high impedance and the low impedance of the scalp to form the current path without the necessity of a wire. Since the present invention does not use a subcutaneous wire to connect the implants, it represents a novel approach to the stimulation technique, and has significant advantages over prior art, since a wire would need to be tunneled under the skin to connect the two implants, requiring additional time in surgery. In addition, current through the scalp may provide the patient with feedback (e.g., a tingling sensation), indicating that current is flowing and stimulation is being administered.

U.S. Patent Application No. 2011/0112602 and 2011/0046693 (Lee) are both directed at using an external magnetic field to induce a current in a subcutaneous coil, with a long probe that extends into the cerebral nerve of the patient to provide DBS. The patents are specific to DBS and only provide for a single probe to proceed through the skull. Since the present invention provides for two or more probes, it is a novel approach that allows for stimulation of a greater number of locations either at the cortex (if the probes are short and just touch the cortex), or deeper in the brain (if the probes are longer and extend into the brain). This has significant advantages over the prior art, since the stimulation site may cover a wider area than a single probe would allow, and two probes allow for better control of the stimulation, ensuring that current proceeds through the brain and not along the probe from one electrode to the other.

U.S. Pat. No. 6,205,359 (Boveja) is directed at treating epilepsy using an implantable coil and lead that is electrically attached to the Vagus nerve. Stimulation is achieved by activating a coil above the surface of the skin which induces current in the implantable coil that provides electric current for stimulation. This patent is directed at Vagus nerve stimulation. It does not mention direct stimulation of the brain. The stimulation provided by the present invention represents a novel approach that has advantages over Vagus nerve stimulation, since the current is applied to the cortical site more directly, with a better understood method of action.

U.S. Patent Application No. 2010/0324623 is directed at tDCS in which probes pierce the skull to provide direct stimulation to the cortex, removing the skull impedance from the path, allowing for greater stimulation current. This patent uses two probes that are stimulated electrically. The probes have an external portion, outside the skin, and an internal portion that proceeds to the cortex. The present invention is a novel approach in that it removes the skull's impedance from the current path, and actually uses the skull's high impedance to create a current loop, allowing stimulation current to be directed at a location in the brain. The present invention has an advantage over the prior art in that it is less invasive, with less pain to the patient, and less chance of infection.

SUMMARY OF THE INVENTION

In broad terms, the present invention provides electrical stimulation to the brain of a person, and comprises at least one implantable portion which generates an electric current, and provides for a conductive path through the skull in at least two locations, using the skull's high impedance to create a current loop which allows current to flow interior and exterior to the skull and through at least one stimulation target.

At least one implantable device may be battery powered or powered externally. In one aspect, the invention comprises at least one external portion, which transfers power to at least one internal portion in order to generate the electrical current for stimulation. The external portion may generate an alternating magnetic field, an ultrasonic sound wave, an RF signal, or another energy generating means.

In one aspect of the device, at least one external portion generates an alternating magnetic field and the at least one internal portion comprises a conductive coil, in order to allow transfer of energy through magnetic induction. The magnetic field will have a primary frequency. In one aspect, the generated magnetic field is approximately between 1 Hz and 20 Hz. In one aspect, the generated magnetic field is approximately between 20 Hz and 100 Hz. In one aspect, the generated magnetic field is approximately between 100 Hz and 500 Hz. In one aspect, the generated magnetic field is approximately between 500 Hz and 5000 Hz. In one aspect, the generated magnetic field is greater than 5000 Hz.

In one aspect of the device, at least one implant portion has a conductive coil that lies between the skull and scalp, and includes a probe which at least partially penetrates the skull with a subcranial electrode at or near the probe tip, and a second subcutaneous electrode between the skull and scalp, where current flows between the two electrodes. In this case, a resistive barrier should surround the probe and fill the space in the burr hole so that current does not shunt between the subcranial electrode and the subcutaneous electrode, but is instead forced to go substantially through the second conductive path.

The alternating magnetic field may be generated either electrically or with permanent magnets. In one aspect of the device, a magnetic field is generated by rotating at least one permanent magnet in at least one external portion. In one aspect of the device, a magnetic field is generated by sending electric current through at least one conductive coil in at least one external portion.

There may be one or more implantable portions. In one aspect, the device comprises a single implantable portion, where the second conductive path consists of a burr hole filled with conductive fluid. Examples of such fluid include but are not limited to cerebrospinal fluid (CST), blood, and saline.

In one aspect, the device comprises two implantable portions. In this case, the electrical current loop proceeds through one probe, through the brain, through the second probe, and back through the scalp to the first electrode.

Current flow through the scalp may cause a sensation that is felt by the person, such as tingling or pain. In one aspect, the magnetic field is generated by rotating at least one permanent magnet in at least one external portion, and the subcutaneous electrodes of the two implantable portions are replaced by a conductive wire that connects the two implantable portions together. A wire would also lower the overall impedance of the current loop, allowing for more current to flow and would remove the potential for a single implantable portion to shunt current from its subcranial electrode, through the burr bole, and back to its subcutaneous electrode.

In one aspect of the device, the implantable portions comprise one implantable portion with a conductive coil and one implantable portion without a conductive coil. The external portion is placed so that the magnetic field is brought in the vicinity of the implantable portion with the conductive coil.

In one aspect of the device, the implantable portions comprise two implantable portions each with a conductive coil. In this case, the external portion could incorporate two magnetic field generating means to apply a magnetic field to each coil or use a single magnetic field generating means to supply power to both implantable coils. Using two coils has the potential to increase the amplitude of current flow through the brain. Two separate external portions could be used to apply a magnetic field to each coil, or a single external portion could be used to apply a magnetic field to only one of the internal portions. In this case, the other implantable portion's coil would act as a passive conductor.

The induced electric current in the coil of an implantable portion is directly proportional to the change in magnetic field over time. Therefore, the faster the magnetic field changes, the higher the change in magnetic field over time, and the greater the induced current in the coil. In one aspect, the magnetic field is approximately sinusoidal. In one aspect, the magnetic field is approximately pulsatile.

Using external portion that generates a magnetic field at high frequency, it may be possible to induce a significant current in the coil of at least one implantable portion, and therefore pass a high current into the brain of a person. This is not always desirable. In one aspect, at least one implantable portion comprises circuitry to limit the maximum current delivered to the person.

In one aspect, the current between the implantable portions alternates at a frequency equal to the magnetic field frequency. However, circuitry could be put in place in one or more implantable portions to allow other stimulation waveforms. In one aspect of the device, an AC to DC converter is in place that allows DC stimulation of the brain, even though the external portion generates an alternating magnetic field.

It may not be desirable to provide electrical stimulation to the brain of a person if the magnetic field is not being generated by an external portion, such as the magnetic field generated by metal detectors. In one aspect, at least one implantable portion with a coil comprises a band-pass filter that will lessen or eliminate the stimulation current if the magnetic field is outside a specified band.

It may also be desirable to administer current pulses to the brain of a person. In one aspect, at least one implantable portion with a coil comprises an energy storage module, a current or voltage gating means, and control logic in order to deliver current pulses.

In one aspect of the device, at least one implantable portion comprises a speaker or vibration means to indicate when the external portion is positioned correctly. This will allow the person or caregiver feedback when applying stimulation, and will give an indication when stimulation is being delivered.

It may be possible for at least one implantable portion to record an EEG. In one aspect of the device, at least one implantable portion comprises an EEG recording means. The EEG recording may be used to determine when to administer electrical stimulation. In one aspect of the device, stimulation is delivered based upon the presence or absence of abnormalities in the EEG waveform. For example, in epilepsy, the device may administer electrical stimulation when a seizure is imminent, as evidenced by spikes in the EEC waveform.

In one aspect of the device, the EEC recording is transmitted by at least one implantable portion wirelessly through the coil and is received by an external portion comprising a conductive coil and a recording means. This would allow the display or analysis of the EEG waveform detected by the implantable portion. The EEG recording may also be transmitted by encoding the information in the gated electrical pulses, which are sensed by electrodes placed on the skin of the person.

In one aspect of the device, the device is used for the treatment of at least one of epilepsy, depression, Parkinson's disease, migraine, fibromyalgia, and stroke rehabilitation.

In one aspect of the device, the device is used to treat migraine and the subcranial electrodes of the implantable portions are located near the visual cortex of the person. In one aspect of the device, the device is used to treat migraine and the subcutaneous electrodes of the implantable portions are located near the occipital nerves of the person. It is also possible to have the subcranial electrodes near the visual cortex and the subcutaneous electrodes near the occipital nerves, thereby achieving the benefit of both mechanisms of action.

In one aspect of the device, the device is used to treat epilepsy and the subcranial electrodes of the implantable portions are located near the epileptic focus in the brain of the person. This epileptic focus may be found through examination of the person's EEG, or by other means.

A method is presented in which electrical stimulation to the cortex of the brain of a person, wherein at least two conductive paths are created through the skull and a current generating means allows the formation of a current loop that runs interior and exterior to the skull of the person.

In one aspect of the method, the power for electrical stimulation is internal to the body of the person. This could be accomplished with an implantable pulse generator and lead, where the pulse generator is implanted, for example, near or beneath the clavicle of the person.

In one aspect of the method, the power for electrical stimulation is external to the body of the person. This could be accomplished, for example, using a handheld magnetic field generator, RF generator, or ultrasonic transducer.

In one aspect of the method, the person or caregiver controls the stimulation by bringing an external energy source on or near the scalp and activating the energy source.

In one aspect of the method, the device is used to treat epilepsy and the person or caregiver activates the magnetic field and brings it in the vicinity of at least one coil in an implanted portion when the person experiences an "aura" associated with an epileptic episode.

In one aspect of the method, the device is used to treat migraine and the person or caregiver activates the magnetic field and brings it in the vicinity of at least one coil in an implanted portion when the person experiences an "aura" associated with an migraine episode.

In addition to treatment based upon specific events, treatment could be administered on a regular basis. In one aspect of the method, the person or caregiver activates stimulation at regular intervals irrespective of symptoms.

Thus, a particular device for electrical stimulation of a person's brain in accordance with the present invention comprise a first conductor implantable through the person's skull at a first location and configured to have a subcutaneous portion over the skull and a subcranial portion which at least partially penetrates the skull to electrically couple with the brain. A second conductor is implantable through the person's skull at a second location spaced-apart from the first location and is configured to have a subcutaneous portion over the skull and a subcranial portion which at least partially penetrates the skull to electrically couple with the brain. An alternating current generator is coupled to one of the first and second conductors so that the first and second conductors will provide a conductive path through the skull in said two locations. The skull's high impedance completes a current loop which allows current to flow interior and exterior to the skull and through at least one stimulation target.

In some embodiments, a coil is coupled to at least one of the conductors, and the current generator is located external to the person's body and generates an alternating magnetic field and transfers energy to the coil through induction. In other embodiments, the alternating current generator comprises a pulse generator coupled to at least one of the conductors, where the pulsed generator transfers energy to the coil through conduction.

Regardless of its specific nature, the alternating current generator may operate at a frequency between 1 Hz and 20 Hz, at a frequency between 20 Hz and 100 Hz, at a frequency between 100 Hz and 500 Hz, at a frequency between 500 Hz and 5000 Hz, or at a frequency greater than 5000 Hz.

In a specific embodiment, the coil is configured to lie over the skull and beneath the scalp and is attached to one of the conductors which is configured to at least partially penetrate the skull through a burr hole. A subcranial electrode is disposed at or near a distal tip of the conductor. Another of the conductors is configured to have a proximal end which lies over the skull and beneath the scalp and at least partially penetrate the skull through a burr hole, also having a subcranial electrode at or near a distal tip thereof. A resistive barrier surrounds the conductor attached to the coil and is configured to fill the burr hole such that electric current is not allowed to shunt between the subcranial electrode and the external portion of the conductor when current flows between the two conductors.

In some embodiments, one of the conductors comprises a conductive fluid configured to fill one of the burr holes. In still other embodiments, a conductive wire that connects the subcutaneous portions of the conductors together. In yet other embodiments, a first conductor comprises one implantable portion with a conductive coil and a second conductor with one implantable portion without a conductive coil, wherein the implantable portion without the conductive coil provides a conductive path through the skull.

The current generator may take a variety of forms. In some instances, the current generator comprises a permanent magnet rotating in close proximity to the conductive coil. In other embodiments, where each conductor comprises a conductive coil, the current generator may comprise two permanent magnets each rotating in close proximity to a conductive coil.

Other features which may be combined with many or allow the embodiments described previously include circuitry to limit the maximum current delivered to the person, an AC to DC converter, an DC to AC converter, an energy storage module, a current or voltage gating means, and control logic in order to deliver current pulses, a speaker or vibration means to indicate to the person or caregiver when the external portion is positioned correctly, and/or an EEG recording means. The EEG recording may be transmitted by at least one implantable portion wirelessly through the coil to be received by an external portion comprising a conductive coil and a recording means. Alternatively, the EEG recording is transmitted by encoding the information in the gated electrical pulses, which are sensed by electrodes placed on the skin of the person.

Particular methods according to the present invention for electrically stimulating a brain of a person comprise for electrically stimulating, a brain of a person, said method comprising. A current flow is generated through said paths, wherein the current flows from a first of the conductive paths to a second of the conductive paths through a further path exterior of the skull and flows back from the second of the conductive paths to the first of the conductive paths through at least one stimulation target in the brain.

The current flow may be generated in a number of ways. The current flow may be generated internally in or externally of the body of the person. The current flow may be generated by bringing an energy source on or near the scalp of the person and activating the energy source. The current flow may be generated by rotating at least one permanent magnet in at least one external portion, or the current flow may be generated by sending electric current through at least one conductive coil in at least one external portion.

The methods of the present invention are useful for treating a number of diseases and condition including epilepsy, Parkinson's disease, migraine, fibromyalgia, and stroke rehabilitation. In particular, the methods may comprise selecting a patient at risk of suffering an epileptic seizure and treating the patient when the person experiences an "aura" associated with an epileptic episode. The methods may comprise selecting a patient at risk of suffering a migraine and treating the patient when the person experiences an "aura" associated with a migraine. The methods may comprise selecting a patient at risk of suffering a migraine and treating the patient at regular intervals irrespective of symptoms. The methods may comprise selecting a patient at risk of suffering a migraine and treating the patient at regular intervals irrespective of symptoms. The methods may be used to treat migraine and at least one target of electrical stimulation is located near the visual cortex of the person. The methods may be used to treat migraine and at least one target of electrical stimulation is located near the occipital nerves of the person. The methods may be used to treat epilepsy and at least one target of electrical stimulation is located near the epileptic focus in the brain of the person.

DETAILED DESCRIPTION OF THE INVENTION

While certain embodiments have been provided and described herein, it will be readily apparent to those skilled in the art that such embodiments are provided by way of example only. It should be understood that various alternatives to the embodiments described herein may be employed, and are part of the invention described herein.

Provided herein is a method and device whereby electrical current stimulation is applied to the brain of a person through one or more conductive paths that proceed through the skull, using the skull's high impedance to create a current loop, which allows current to flow interior and exterior to the skull and through at least one stimulation target.

In one aspect, the device comprises at least one external portion and at least one implantable portion. The external portion provides energy to the implantable portions through at least one of an alternating magnetic field, an ultrasonic sound wave, RF generator or another energy generating means. Each implantable portion may contain a conductive probe that goes at least partially through the skull, forming a conductive path from the subcutaneous space to the subcranial space. At least one of the implantable portions comprises a means to convert the energy from the external portion into electric current. In one aspect, this means comprises a coil, which creates a current when an external alternating magnetic field is brought in close proximity to the coil.

In one aspect with two implants (Implant #1 and Implant #2), the current forms a loop that proceeds from the current generating means in Implant #1, through implant #1's probe which at least partially penetrates the skull, through the subcranial electrode of implant #1, through the brain of the person, through the subcranial electrode of implant through implant #2's probe which at least partially penetrates the skull, through the subcutaneous electrode of implant #2, through or under the person's scalp, back to the subcutaneous electrode of implant #, and back to implant current generating means.

Figure 1:
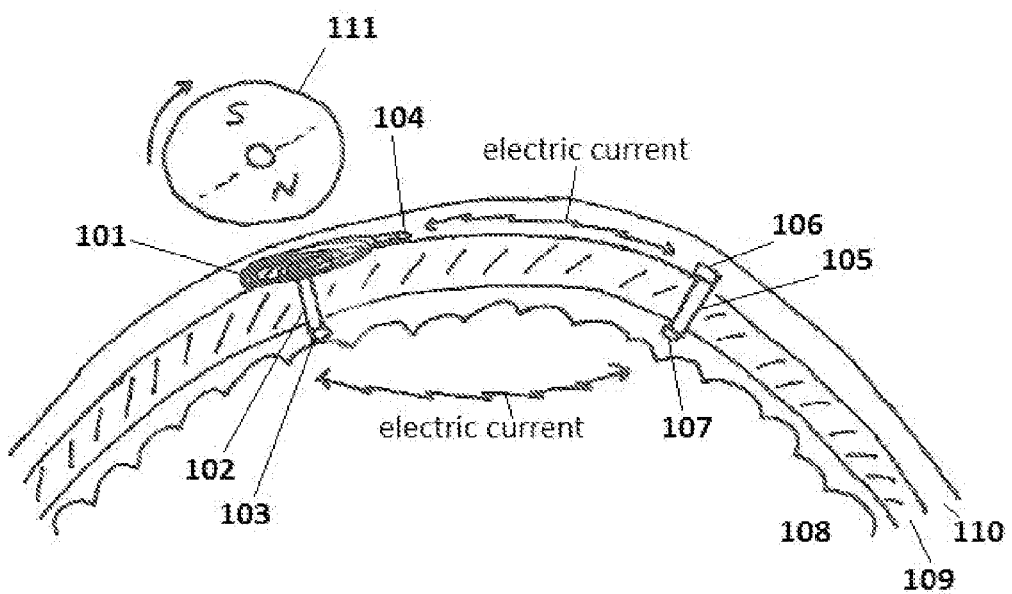
FIG. 1 is a drawing of one aspect of the device, in which a magnet is rotated above an implantable portion with a coil, and a current loop is formed between the implantable portion with a coil and the implantable portion without a coil.

With reference to FIG. 1, a drawing is shown which represents a typical application of the present device. When the magnet (111) is rotated, an alternating magnetic field is generated. When the magnetic field is brought in close proximity to the coil (101), an electric current is induced which travels through the probe (102) and creates a voltage potential between the subcutaneous electrode (104) and the subcranial electrode (103). The probe is surrounded by a resistive barrier that fills the burr hole to prevent electric current from being shunted between the subcutaneous electrode and the subcranial electrode. The skull has high electrical resistivity, which is generally 80 times the resistivity of the cerebrospinal fluid (CSF). Therefore, a portion of current flowing between the two electrodes (103, 104) will proceed through the brain (108) to other implantable portion, flowing through the subcranial electrode (107), the probe (105), and the subcutaneous electrode (106), completing a loop through or beneath the scalp (110) back to the subcutaneous electrode (104). In this drawing, the probes extend fully through the skull and are at or near the surface of the brain. However, the probes could be a variety of lengths, including only partially penetrating the skull.

Having the current loop use the subcutaneous space through or beneath the scalp as a conductor may result in stimulation of peripheral nerves in the region. In one aspect of the device, the subcutaneous electrodes are used to stimulate the occipital nerves. Occipital nerve stimulation (ONS) has been shown to be efficacious in treatment of migraine. In one aspect of the device, the subcutaneous electrodes are used to stimulate the trigeminal nerves. Stimulation of the trigeminal nerves on the forehead has been shown to be efficacious in treatment of epilepsy, depression, attention deficit hyperactivity disorder (ADHD), and post-traumatic stress disorder (PTSD).

Figure 2:
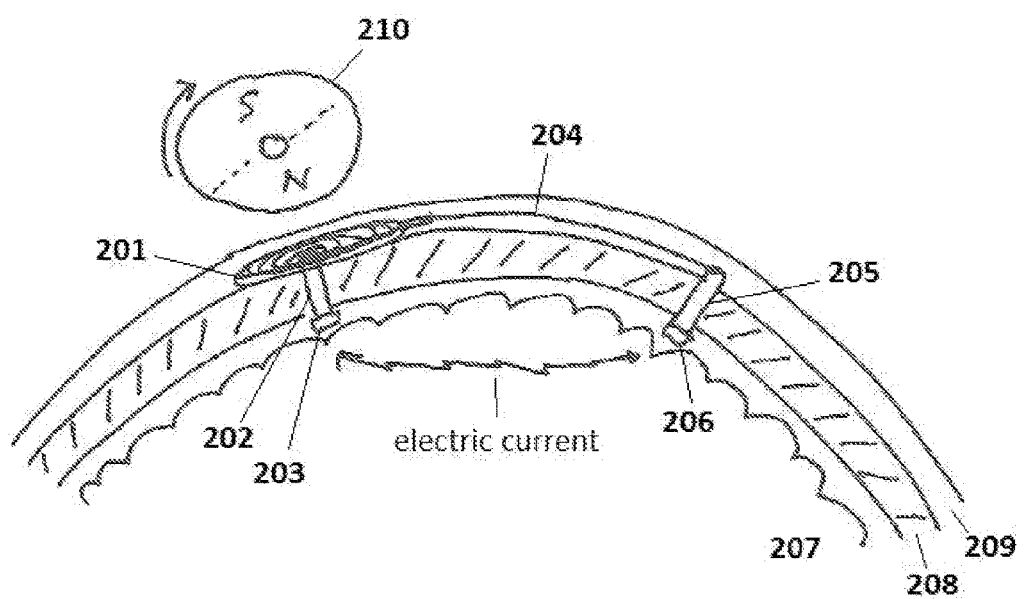
FIG. 2 is a drawing of one aspect of the device, in which a magnet is rotated above an implantable portion with a coil, and a current loop is formed between the implantable portion with a coil and the implantable portion without a coil, where the subcutaneous electrodes are connected by a wire, preventing stimulation of peripheral nerves.

With reference to FIG. 2, a drawing is shown which represents an alternate aspect of the present device which avoids stimulation of peripheral nerves within or beneath the scalp (209). In this, the magnet (210) rotates, causing an alternating magnetic field to be generated. When the magnetic field is brought in close proximity to the coil (201), an electric current is induced, which travels through the probe (202) that penetrates the skull (208) to the subcranial electrode (203). The current also flows through the wire (204) to the other implantable portion, flowing through the probe (205) and subcranial electrode (206). In this, the primary conductive path between the electrodes (203, 206) is through the brain (207). An advantage of this aspect is that impedance of the scalp does not add to the overall impedance of the system, which may allow tin increased amplitude of current through the brain.

Figure 3:
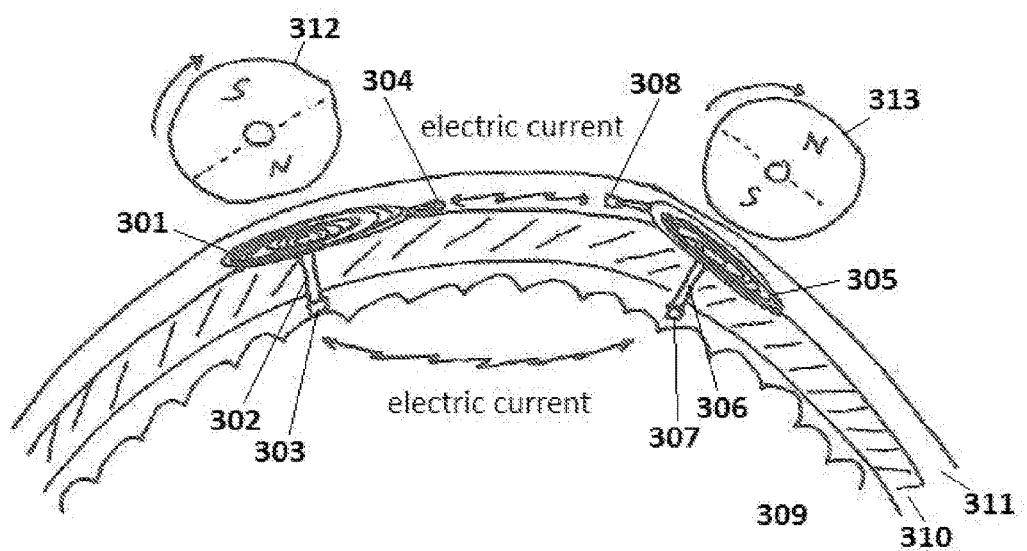
FIG. 3 is a drawing of one aspect of the device, in which two magnets are rotated above two implantable portions with a coil, and a current loop is formed between the implantable portions.

With reference to FIG. 3, a drawing is shown which presents an alternate aspect of the present device, in which two magnets (312, 313) are rotated above two coils (301, 305). The rotating magnets induce current in the two coils, with the current proceeding through the skull (310) via two probes (302, 306). Electric current flows between the two subcutaneous electrodes (304, 308) through or beneath the scalp (311) of the person. Completing the loop, current also flows between the subcranial electrodes (303, 307), with a portion flowing through the brain (309) of the person. By using two magnets instead of one, at greater current may be generated. The magnets need to be rotated with a phase relationship that will result in the induced current from each coil being additive, and not subtractive. This may require more precise placement of the magnets above the scalp of the person. Alternately, one magnet could be rotated over one of the coils, even though more than one implanted coil may be present. In this aspect, only one of the coils will create an induced current. The other coil will remain as a passive conductor, only contributing an inductive effect on the current as it passes through.

Figure 4:
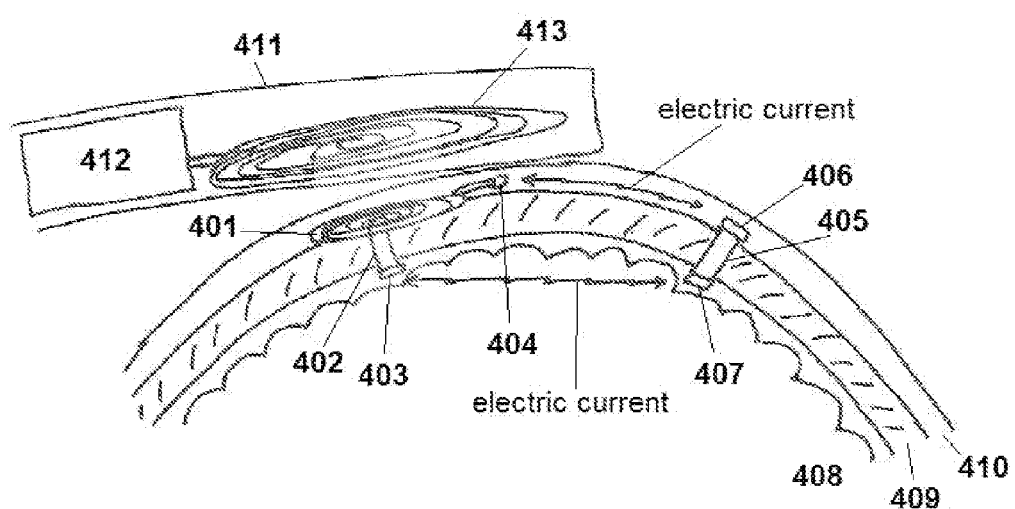
FIG. 4 is a drawing of one aspect of the device, in which the magnetic field is generated by a coil.

With reference to FIG. 4, a drawing is shown which presents an alternate aspect of the present device, in which the magnetic field is generated using a wand (411) that comprises a coil (413) and supporting electronics (412). By generating an alternating electric current through the coil (413), a time varying magnetic field is created. When the magnetic field is brought in close proximity to the coil (401) of an implanted portion, a current is induced in the coil. The current proceeds through the probe (402) that penetrates the skull (409) and creates a voltage potential between the subcutaneous electrode (404) and the subcranial electrode (403). The probe is surrounded b a resistive barrier that fills the burr hole to prevent electric current from being shunted between the subcutaneous electrode and the subcranial electrode. A portion of current flowing between the two electrodes (403, 404) will proceed through the brain (408) to other implantable portion, flowing through the subcranial electrode (407), the probe (405), and the subcutaneous electrode (406), completing a loop through or beneath the scalp (410) back to the subcutaneous electrode (404). By using a wand with a coil to generate the magnetic field, it may be possible to create magnetic field pulses of varying shapes, allowing for varying current pulses to flow in the brain. A coil also has the ability to create a significantly higher change in magnetic field over time, which would allow for significantly higher current amplitudes to be delivered.

Figure 5:
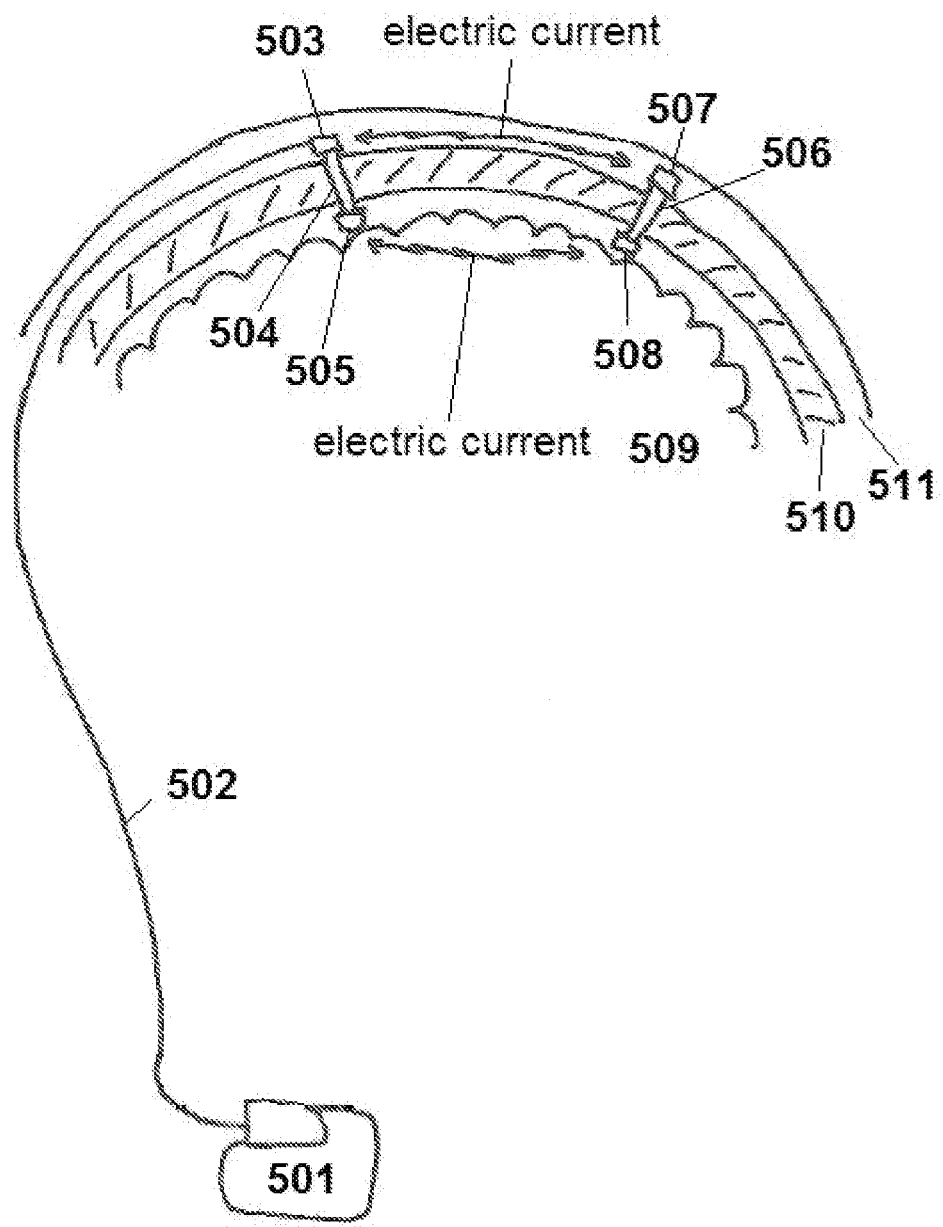
FIG. 5 is a drawing of one aspect of the device, in which the electric current is generated by an implantable pulse generator.

With reference to FIG. 5, a drawing is shown which presents an alternate aspect of the present device, in which the electric current is generated using a pulse generator module (501) that sends an electric current through a lead (502) containing two or more wires. The pulse generator may be located in the torso of the person with the lead wire fed up to the area of stimulation. The pulse generator may also be located in the head of the person, possibly replacing a portion of the skull removed with a craniotomy. One lead wire is connected to a subcutaneous electrode (503) and the other proceeds through a probe (504) that penetrates the skull (510) and ends in a subcranial electrode (505), such that an electric, voltage potential is created between the two electrodes (503, 505). The probe is surrounded by a resistive barrier that fills the burr hole to prevent electric current from being shunted between the subcutaneous electrode and the subcranial electrode. A portion of current flowing between the two electrodes (503, 505) will proceed through the brain (509) to other implantable portion, flowing through the subcranial electrode (508), the probe (506), and the subcutaneous electrode (507), completing a loop through or beneath the scalp (511) back to the subcutaneous electrode (503). Using an implantable pulse generator has the advantage in that an external portion is not required. In one aspect, current pulses are generated continuously to stimulate an area. In an alternate aspect, the pulse generator is activated by the user, possibly by holding a permanent magnet over the pulse generator and activating a magnetic switch. In an alternate aspect, the pulse generator includes a bio-amplifier to sense the neuronal activity of the brain near the area of stimulation, and only provides pulses when necessary. For example, the device could be used to treat epilepsy, and only be activated when the pulse generator control logic detects abnormal electrocorticographic activity.

Figure 6:
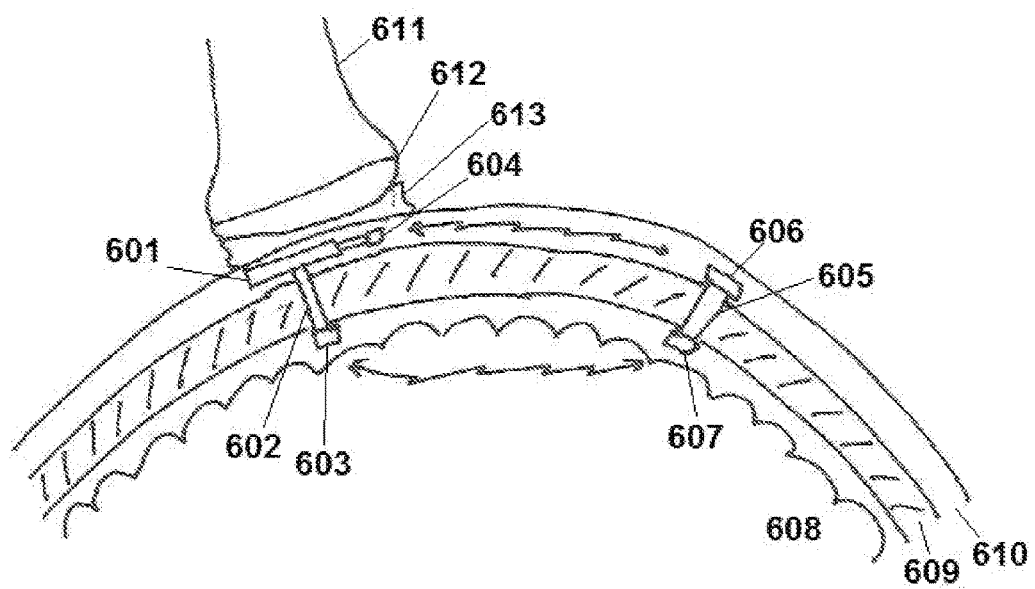
FIG. 6 is a drawing of one aspect of the device, in which the electric current is generated through an ultrasonic transducer, with a handheld ultrasonic transmitter held close to the scalp.

With reference to FIG. 6, a drawing is shown which presents an alternate aspect of the present device, in which the electric current is generated using energy from an ultrasonic transducer. A hand-held ultrasonic generator (611) creates ultrasonic stimulation through a transducer (612) that is placed in the vicinity of an implanted subcutaneous ultrasonic transducer (601). An acoustic gel (613) may be used to improve the efficiency of the system. The implanted ultrasonic transducer (601) and supporting electronics create an electric current. The current proceeds through the probe (602) that penetrates the Skull (609) and creates a voltage potential between the subcutaneous electrode (604) and the subcranial electrode (603). The probe is surrounded by a resistive barrier that fills the burr hole to prevent electric current from being shunted between the subcutaneous electrode and the subcranial electrode. A portion of current flowing between the two electrodes (603, 604) will proceed through the brain (608) to other implantable portion, flowing through the subcranial electrode (607), the probe (605), and the subcutaneous electrode (606), completing a loop through or beneath the scalp (610) back to the subcutaneous electrode (604). The use of an ultrasonic transducer instead of a coil may allow treatment for persons who are unable to withstand large magnetic fields, possibly due to an implantable device implanted in the head. In addition, an ultrasonic transducer may be more easily able to create a DC electric current in the brain, which may be beneficial in the treatment of certain disorders.

Figure 7:
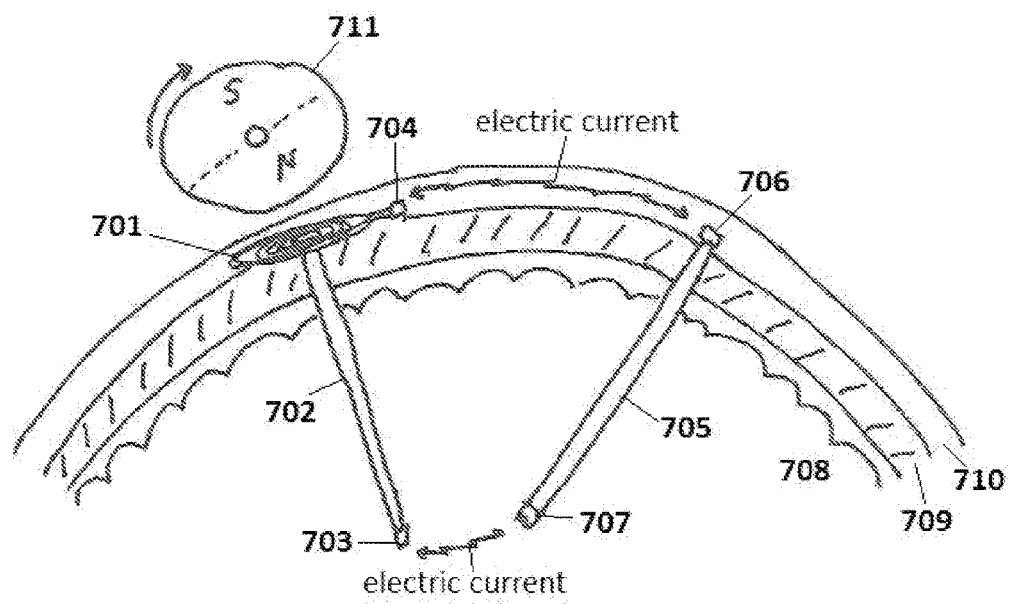
FIG. 7 is a drawing of one aspect of the device, in which the probes of the implantable portion are long and proceed into the interior of the brain, allowing for electrical stimulation of deeper structures.

With reference to FIG. 7, a drawing is shown which presents an alternate aspect of the present device, in which the probes are longer and extend deeper into the brain. When the magnet (711) is rotated, an alternating magnetic field, is generated. When the magnetic field is brought in close proximity to the coil (701), an electric current is induced which travels through the probe (702) and creates a voltage potential between the subcutaneous electrode (704) and the subcranial electrode (703). The probe is surrounded by a resistive barrier that fills the burr hole to prevent electric current from being shunted between the subcutaneous electrode and the subcranial electrode. A portion of current flowing between the two electrodes (703, 704) will proceed through the brain (708) to other implantable portion, flowing through the subcranial electrode (707), the probe (705), and the subcutaneous electrode (706), completing a loop through or beneath the scalp (710) back to the subcutaneous electrode (704). By extending the probes deeper, it is possible to target deep structures in the brain, such as the basal ganglia, cerebellum, anterior principal nucleus, centromedian nucleus, caudate nucleus, thalamic or subthalamic region. It is not necessary for the probes to penetrate the skull at a 90 degree angle or to be completely straight. By bending the probes or changing their length and/or angle relative to the skull, it would be possible to selectively target nearly any area of the brain currently targeted with DBS.

Figure 8:
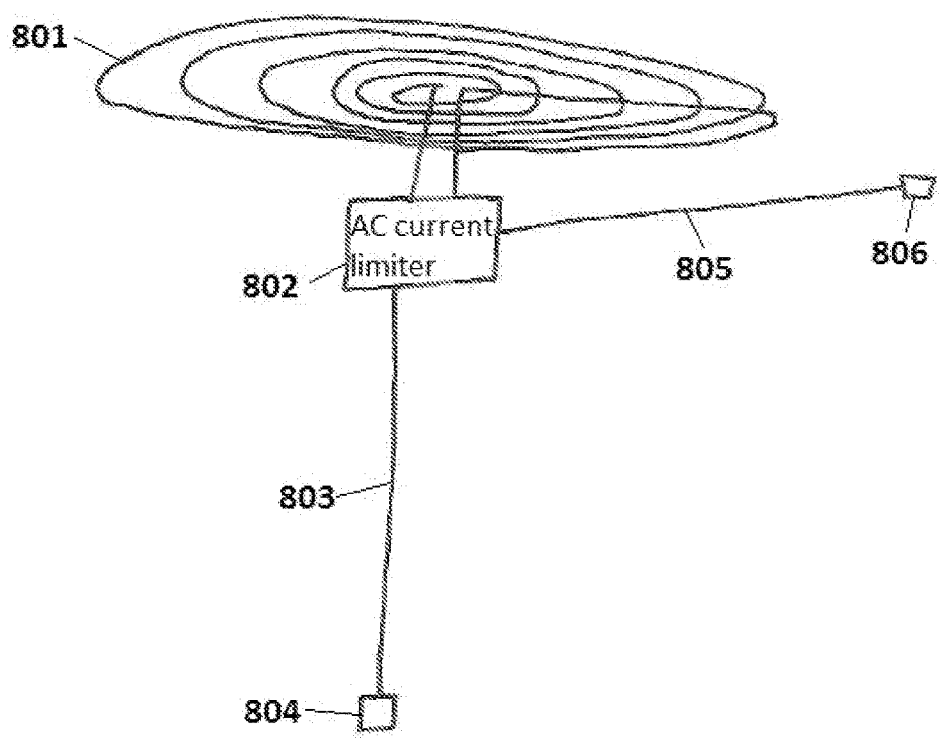
FIG. 8 is a drawing of one aspect of the device, which incorporates an AC current limiter to prevent high currents from entering the brain of the person.

With reference to FIG. 8, a drawing is shown which presents an alternate aspect of the present device, which includes an AC current limiter (802). A magnetic field induces a current in the coil (801). The current limiter will allow current to proceed through the probe (803) to the subcranial electrode (804) and to a wire (805) that extends to the subcutaneous electrode (806). If the current exceeds a specified maximum, the current limiter will shunt some or all of the current or alter the impedance to limit the full induced current delivered to the brain of a person. Using a current limiter is important to protect the brain from high currents and to help prevent or limit pain or adverse effects from the therapy. A typical current limiter may comprise at least one transistor and sense resistor.

Figure 9:
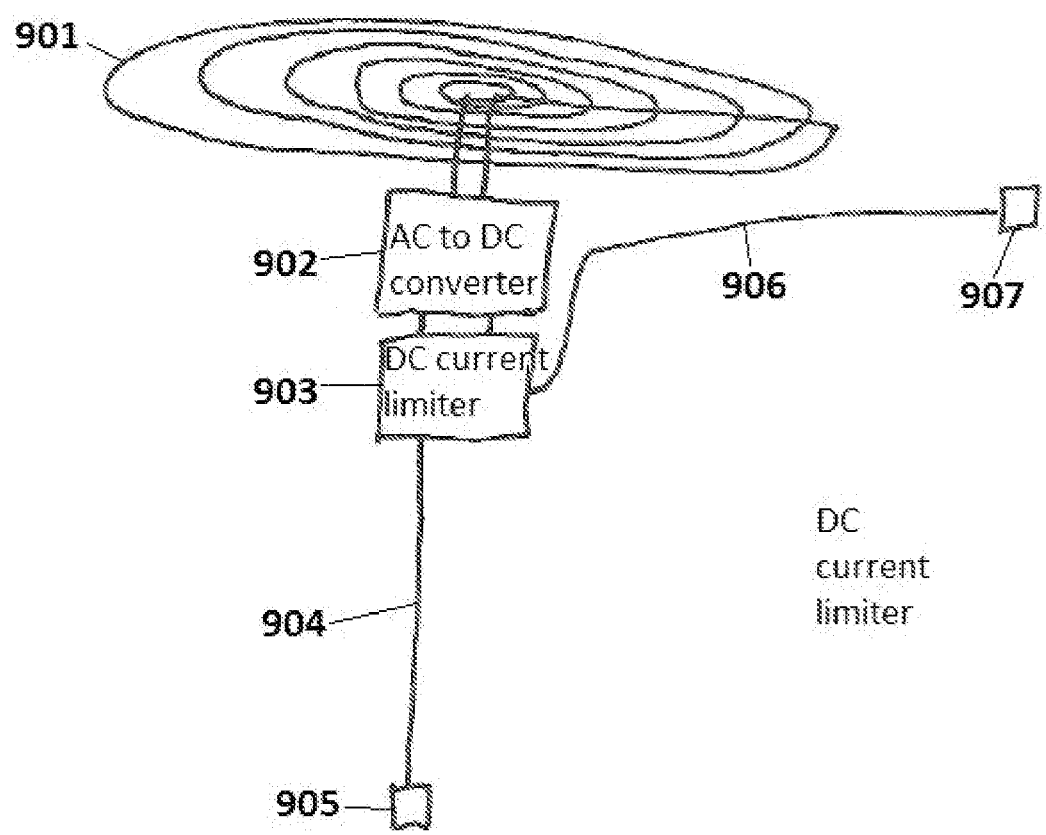
FIG. 9 is a drawing of one aspect of the device, which incorporates an AC to DC converter and DC current limiter which allows for electrical stimulation of the brain with a DC current that is current limited to prevent over stimulating the brain.

With reference to FIG. 9, a drawing is shown which presents an alternate aspect of the present device, which includes an AC to DC converter (902) and a DC current limiter (903). A magnetic field induces a current in the coil (901), The AC to DC converter changes the induced AC current into a DC current. Typically, this may be done using a voltage rectifier and energy storage means, such as a capacitor. The DC current limiter prevents the current from exceeding a specified limit. The current limiter allows current to proceed through the probe (904) to the subcranial electrode (905) and to a wire (906) that extends to the subcutaneous electrode (907). This configuration allows stimulation with a DC current instead of the AC current, and prevents the device from delivering a high current which could adversely affect the therapy or cause pain to the person.

Figure 10:
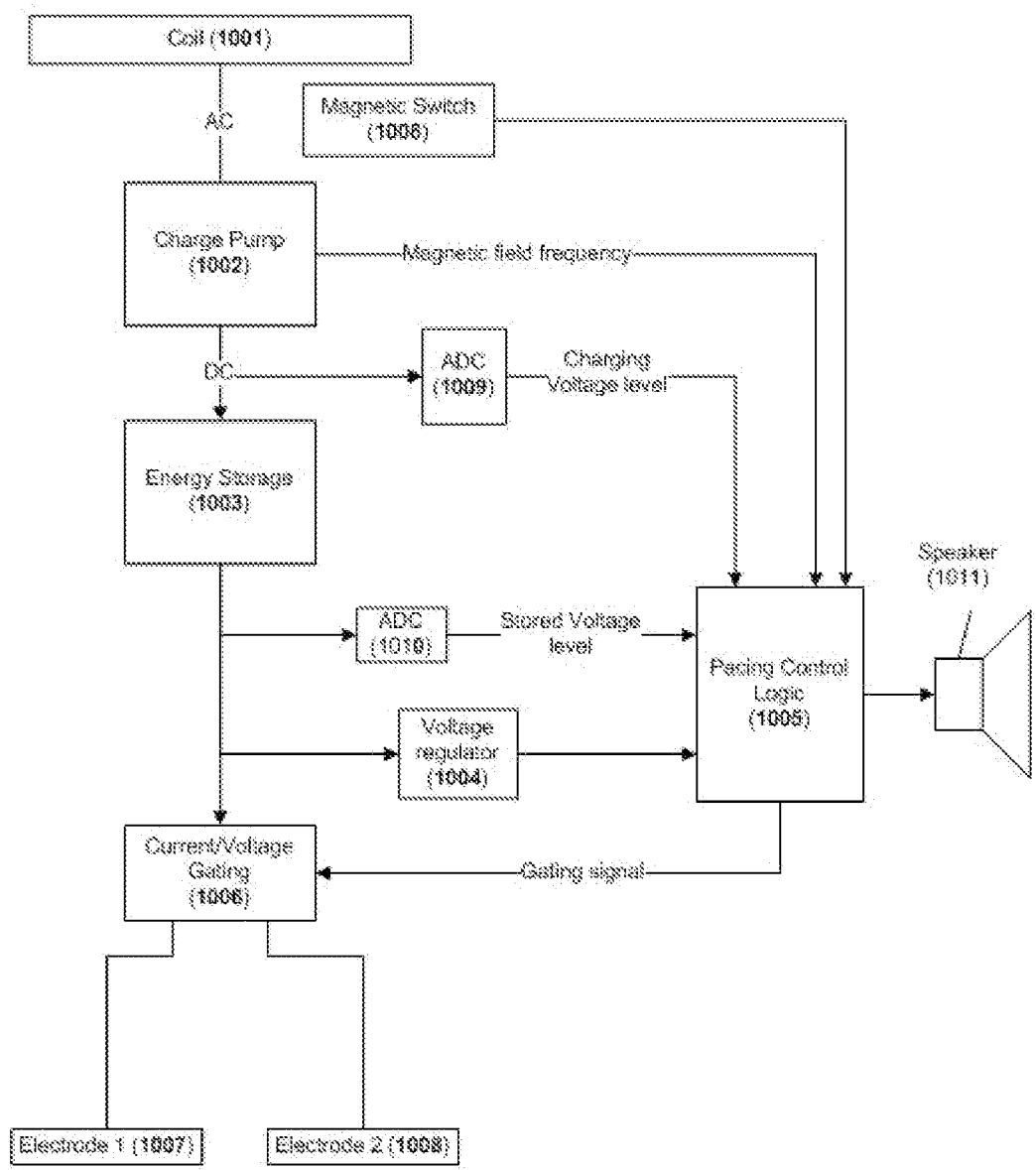
FIG. 10 is a drawing of one aspect of the device, which incorporates a charge pump and energy storage module, along with a current/voltage gating means, control logic, and associated electronics to provide pacing pulses to the brain of the person. A speaker is also included to inform the person or caregiver of proper positioning of the magnetic field.

With reference to FIG. 10, a drawing is shown Which presents an alternate aspect of the present device, in which the implantable portion stores energy and administers pacing pulses until the stored energy is expended. A magnetic field induces a current in the coil (1001), which is used with a charge pump (1002) to charge an energy storage module (1003), which, for example, could be a capacitor or rechargeable battery. The stored voltage energy is used with a voltage regulator (1004) to provide power to the pacing control logic. Pacing control logic sends a gating signal to the Current/Voltage Gating module (1006), which supplies current to the two electrodes (1007, 1008), one of which is the subcutaneous electrode and one of which is the subcranial electrode. The Pacing Control logic samples the stored voltage level using the analog to digital converter (ADC) (1010) to determine when to initiate and terminate pacing. It may also sample the charging voltage level using another ADC (1009) along with the magnetic field frequency from the charge pump to determine when the correct magnetic field is present. This will help prevent inadvertent pacing activation. In addition, a magnetic switch (1008) may be incorporated to detect the presence of a permanent magnet, which will allow the pacing control logic to initiate and terminate pacing based upon the presence or absence of a magnetic field. The device could optionally use a speaker (1001) to inform the user when pacing is being administered. This could be used to ensure that external magnetic field generator is in the correct position, and to allow the person an indication that therapy is being administered. When the alternating magnetic field is removed and the energy storage module is no longer being charged, the pacing control logic may cease administering therapy. When the voltage in the energy storage module drops below the minimum necessary to supply adequate power to the pacing control logic, the device could shut down completely until the alternating magnetic field is applied again.

Figure 11:
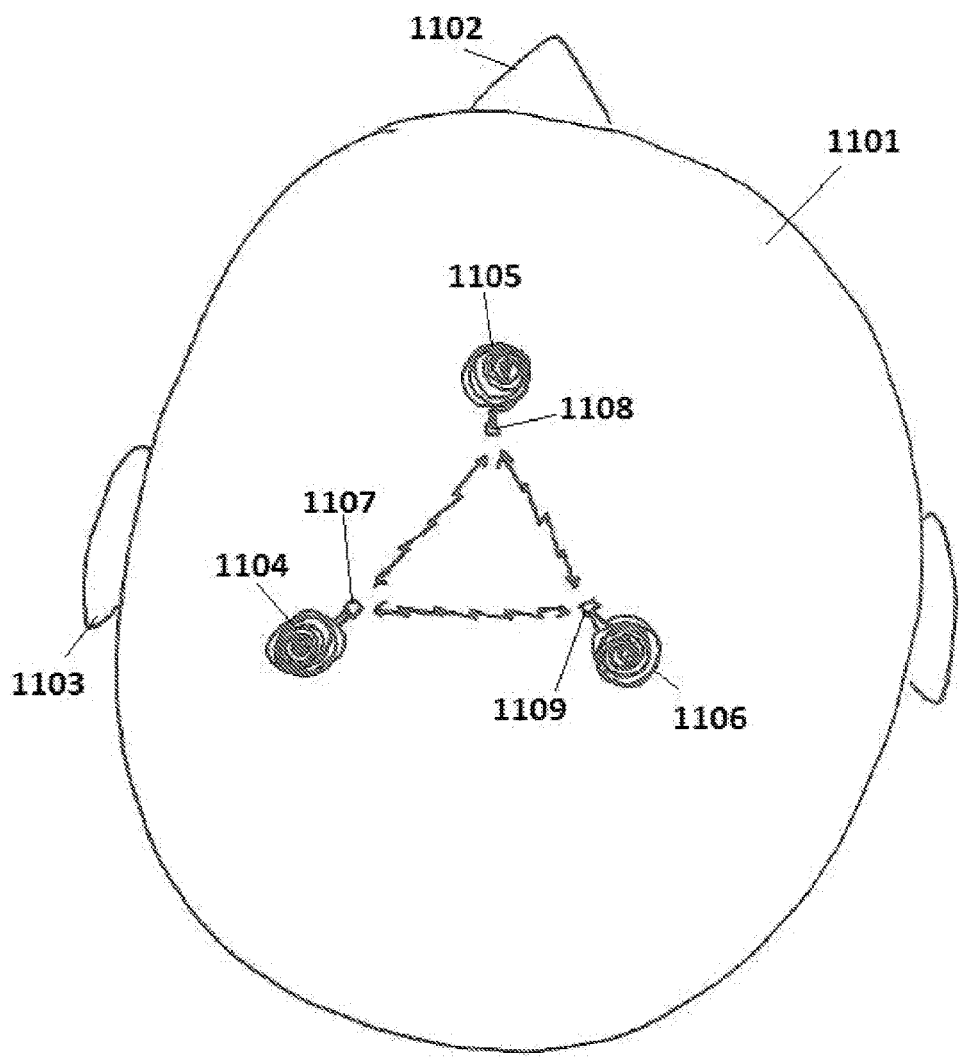
FIG. 11 is a drawing of one aspect of the device, in which three implantable portions are used, each of them with a coil. This allows electric current to flow through multiple areas of the brain when a magnetic field is present.

With reference to FIG. 11, a drawing is shown which presents an alternate aspect of the present device, which comprises three implantable portions in the head (1101) of a subject. The diagram shows the nose (1102) and ears (1103) for reference. An external magnetic field may be located in the vicinity of one or more of the three coils (1104, 1105, 1106) to induce an electric current. The electric current will flow between the three subcutaneous electrodes (1107, 1108, 1109) and the three subcranial electrodes (not shown), thereby stimulating multiple regions according to the electrode placement. Stimulation of multiple regions may be desirable in certain disorders that affect more than one brain region.

Figure 12:
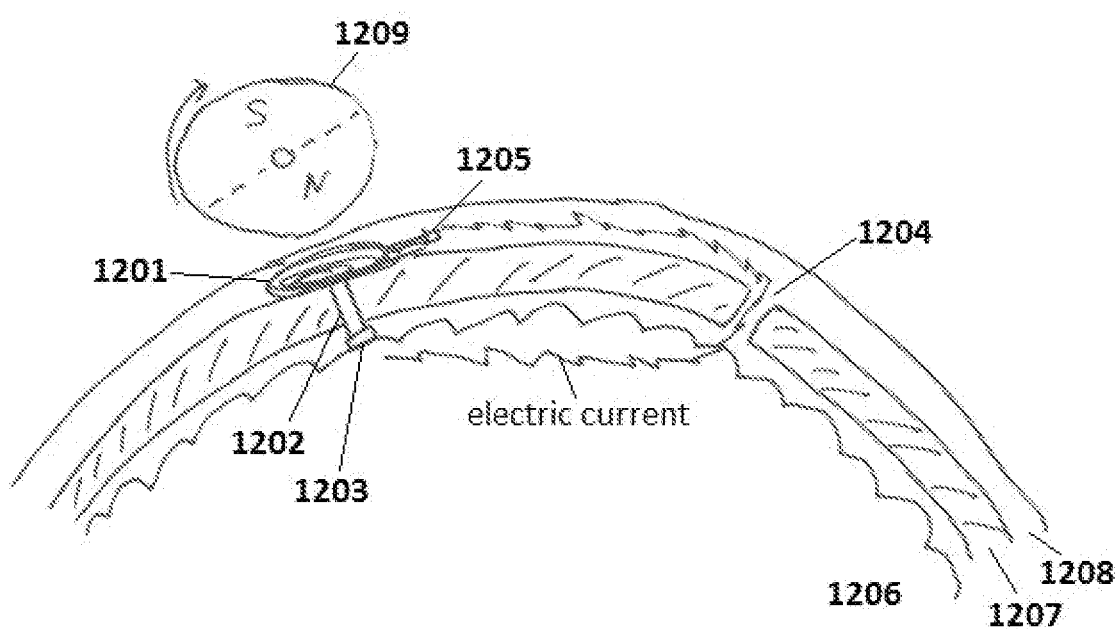
FIG. 12 is a drawing of one aspect of the device, in which a single implantable portion is used. Instead of using a second probe, the current loop proceeds through the burr hole that is filled with fluids such as CSF.

With reference to FIG. 12, a drawing is shown which presents an alternate aspect of the present device, which comprises a single implantable portion. When the magnet (1209) is rotated, an alternating magnetic field is generated. When the magnetic field is brought in close proximity to the coil (1201), an electric current is induced which travels through the probe (1202) and creates a voltage potential between the subcutaneous electrode (1205) and the subcranial electrode (1203). The probe is surrounded by a resistive barrier that fills the burr hole to prevent electric current from being shunted between the subcutaneous electrode and the subcranial electrode. The skull has high electrical resistivity, which is generally 80 times the resistivity of the cerebrospinal fluid (CSF). Therefore, a portion of current flowing between the two electrodes (103, 104) will proceed through the brain to a second burr hole (1204) that is naturally tilled with fluid such as CSF, which allows current to flow back through the skull to the scalp back to the subcutaneous electrode (1205), completing the current loop.

In one aspect of the device, the person carries the external portion with them and activates the external portion, placing it in the vicinity of one or more coils, thereby self-administering treatment.

In one aspect of the device, a nurse or caregiver administers treatment by activating the external magnetic field in the vicinity of one or more coils.

In one aspect of the device, treatment is used for at least one of epilepsy, depression, Parkinson's disease, migraine, fibromyalgia, and stroke rehabilitation.

In one aspect of the device, treatment for epilepsy is administered when the subject perceives an "aura" that precedes the event.

In one aspect of the device, treatment for migraine is administered when the subject perceives an "aura" that precedes the event.

In one aspect of the device, the external portion is incorporated into a hat, strap, or headband that can be worn by the person, thereby keeping the external portion in the correct position for long periods of time. This may allow longer periods of uninterrupted stimulation.

In one aspect of the device, the internal portion incorporates a speaker, vibration means, or other means to inform at least one of the person and caregiver whether the external portion is in the correct location or stimulation is being delivered.

In one aspect of the device, the magnetic field frequency is approximately between 1-20 Hz. In one aspect of the device, the magnetic field frequency is approximately between 20-100 Hz. In one aspect of the device, the magnetic field frequency is approximately between 100 Hz and 500 Hz. In one aspect of the device, the magnetic field frequency is approximately between 500 Hz and 1000 Hz. In one aspect of the device, the magnetic field frequency is greater than 5000 Hz.

In one aspect of the device, the electric current administered to the brain is DC. In one aspect of the device, the electric current administered to the brain is a harmonic of the magnetic field frequency.

In one aspect of the device, at least one implantable portion comprises an EEG amplifier, which records EEG signals between the subcutaneous electrode and subcranial electrode, and includes logic which controls when electrical stimulation is provided, to the brain of a person, based upon abnormalities in the EEG signal. For example, the implant could provide stimulation to a person with epilepsy when the EEG shows that a seizure is imminent, such as when spikes appear on the recording. The logic may also prohibit stimulation based upon the absence of abnormalities in the EEG signal. For example, if the person with epilepsy attempts to self-administer treatment, the implant could prohibit stimulation if it is found that a seizure is not imminent.

In one aspect of the device, at least one implantable portion incorporates a rechargeable energy storage unit, such as a battery or capacitor, which is charged when the alternating magnetic field is present, and maintains that charge after the magnetic field is removed. This energy storage unit provides power to an EEG amplifier and recording logic. The purpose is to record EEG signals between the subcutaneous electrode and subcranial electrode, and includes logic which controls when electrical stimulation is provided to the brain of a person, based upon potential abnormalities in the EEG signal. For example, the implant could provide stimulation to a person with epilepsy when the EEG shows that a seizure is imminent, such as when spikes appear on the recording. In this case, the enemy from the enemy storage unit is used to provide electrical stimulation to the brain of the person.

In one aspect of the device, at least one implantable portion incorporates a rechargeable energy storage unit, such as a battery or capacitor, which is charged when the alternating magnetic field is present, and maintains that charge after the magnetic field is removed. The energy storage unit provides power to allow for regular electrical stimulation of the brain. For example, the energy storage unit may provide an electrical pulse once per second, once per minute, or at other intervals in order to affect the brain. It has been shown that regular stimulation of neurons has a de-sensitizing effect that lasts beyond the end of stimulation. In one aspect of the device, the epileptic focus could be stimulated at regular intervals to reduce or eliminate seizures.

What is claimed is:

1. A device for electrical stimulation of a person's brain, the device comprising:
    a first conductor implantable through the person's skull at a first location and configured to have a subcutaneous portion over the skull and a suberanial portion which at least partially penetrates the skull to electrically couple with the brain;
    a second conductor implantable through the person's skull at a second location spaced-apart from the first location and configured to have a subcutaneous portion over the skull and a subcranial portion which at least partially penetrates the skull to electrically couple with the brain;
    an alternating current generator coupled to one of the first and second conductors, wherein the first and second conductors provide a conductive path through the skull in said two locations and the skull's high impedance completes a current loop which allows current to flow interior and exterior to the skull and through at least one stimulation target, wherein the first conductor comprises one implantable portion with a conductive coil and the second conductor comprises one implantable portion without a conductive coil, wherein the implantable portion without the conductive coil provides a conductive path through the skull.

2. The device of claim 1, wherein the alternating current generator comprises a pulse generator coupled to at least one of the conductors, wherein the pulse generator transfers energy to the coil through conduction.

3. The device of claim 1 wherein the alternating current generator operates at a frequency between 1 Hz and 20 Hz.

4. The device of claim 1, wherein the alternating current generator operates at a frequency between 20 Hz and 100 Hz.

5. The device of claim 1 wherein the alternating current generator operates at a frequency between 100 Hz and 500 Hz.

6. The device of claim 1, where the alternating current generator operates at a frequency between 500 Hz and 5000 Hz.

7. The device of claim 1, wherein the alternating current generator operates at a frequency greater than 5000 Hz.

8. The device of claim 1, wherein the coil is configured to lie over the skull and beneath the scalp and is attached to one of the conductors which is configured to at least partially penetrate the skull through a burr hole with a subcranial electrode at or near a distal tip thereof and wherein another of the conductors is configured to have a proximal end which lies over the skull and beneath the scalp and at least partially penetrate the skull through a burr hole with a subcranial electrode at or near a distal tip thereof, further including a resistive barrier surrounding the conductor attached to the coil and configured to fill the burr hole such that electric current is not allowed to shunt between the subcranial electrode and the external portion of the conductor when current flows between the two conductors.

9. The device of claim 1, further comprising a conductive wire that connects the subcutaneous portions of the conductors together.

10. The device of claim 1, wherein the current generator comprises a permanent magnet rotating in close proximity to the conductive coil.

11. The device of claim 1, wherein the current generator comprises two permanent magnets each rotating in close proximity to a conductive end.

12. The device of claim 1, further comprising circuitry to limit the maximum current delivered to the person.

13. The device of claim 1, further comprising an AC to DC converter.

14. The device of claim 1, further comprising an DC to AC converter.

15. The device of claim 1, further comprising an energy storage module, a current or voltage gating means, and control logic in order to deliver current pulses.

16. The device of claim 1, further comprising a speaker or vibration means to indicate to the person or caregiver when the external portion is positioned correctly.

17. The device of claim 1, further comprising an EEG recording means.

18. The device of claim 17, wherein the EEG recording is transmitted by at least one implantable portion wirelessly through the coil and is received by an external portion comprising a conductive coil and a recording means.

19. The device of claim 17, wherein the EEG recording is transmitted by encoding the information in the gated electrical pulses which are sensed by electrodes placed on the skin of the person.

* * * * *